United States Patent
Hanai et al.

(10) Patent No.: US 6,180,102 B1
(45) Date of Patent: Jan. 30, 2001

(54) MONOCLONAL ANTIBODY TO HUMAN MX PROTEIN MXA

(75) Inventors: Nobuo Hanai; Kyosuke Nagata, both of Kanagawa; Akiko Furuya, Tokyo; Akira Kusano, Kanagawa; Noboru Taniguchi, Ishikawa, all of (JP)

(73) Assignees: Kyowa Hakko Kogyo Co., Ltd.; Kyowa Medex Co., Ltd., both of Tokyo (JP)

( * ) Notice: Under 35 U.S.C. 154(b), the term of this patent shall be extended for 0 days.

(21) Appl. No.: 09/165,798

(22) Filed: Oct. 2, 1998

Related U.S. Application Data

(63) Continuation of application No. 08/628,612, filed as application No. PCT/JP95/01573 on Aug. 8, 1995, now abandoned.

(30) Foreign Application Priority Data

Aug. 8, 1994 (JP) .................................... 6-185817
Aug. 8, 1995 (WO) .................................... PCT/JP95/01573

(51) Int. Cl.$^7$ ........................ A61K 39/395; A61K 39/42; C12P 21/04; C12N 5/06
(52) U.S. Cl. .................................... 424/152.1; 424/130.1; 424/139.1; 424/141.1; 424/145.1; 424/158.1; 435/5; 435/7.1; 435/70.2; 435/70.21; 435/326; 530/388.1; 530/386.2; 530/809
(58) Field of Search ............................ 435/5, 7.1, 70.21, 435/70.2, 326; 530/388.2, 388.1, 809; 424/130.1, 139.1, 141.1, 145.1, 152.1, 158.1

(56) References Cited

U.S. PATENT DOCUMENTS

| | | | |
|---|---|---|---|
| 5,198,350 | 3/1993 | Horisberger et al. | 530/388.1 |
| 5,739,290 | * 4/1998 | Horisberger | 530/388.2 |
| 5,869,264 | * 2/1999 | Horisberger | 435/7.1 |

FOREIGN PATENT DOCUMENTS

WO 87/00864  2/1987  (WO).

OTHER PUBLICATIONS

Staeheli et al., "Polyclonal and Monoclonal Antibodies to the Interferon–inducible Protein Mx of Influenza Virus–resistant Mice" Journal of Biological Chemistry (1986) 280 (2) 1821–1826.

Towbin et al, "A Whole Blood Immuoassay for the Interferon–Inducible Human Mx Protein", Journal of Interferon Research 12:67–74 (1992).

Aebi et al, "cDNA Structures and Regulation of Two Interferon–Induced Human Mx Proteins", Molecular and Cellular Biology 9(11):5062–5072 (1989).

Horisberger et al, "IFN–α Induced Human 78 kD Protein: Purification and Homologies with the Mouse Mx Protein, Production of Monoclonal Antibodies, and Potentiation Effect of IFN–γ", Journal of Interferon Research 7:331–343 (1987).

Goetschy et al, J. Virol., 63 (6): 2616–2622, Jun. 1989.

Pitkaranta et al., J. Interferon Research, 11: 17–33, 1991.

* cited by examiner

Primary Examiner—Marianne P. Allen
Assistant Examiner—Mary K Zeman
(74) Attorney, Agent, or Firm—Nixon & Vanderhye P.C.

(57) ABSTRACT

This invention provides a monoclonal antibody which recognizes an epitope corresponding to amino acids 10 to 220, amino acids 221 to 297, or amino acids 469 to 662, counting from the N-terminus of a human Mx protein MxA, and specifically reacts with the human Mx protein by western blotting, immunoprecipitation or immunocyte staining, and a hybridoma which produces the antibody. The human Mx protein MxA monoclonal antibody of this invention can be used, for example, in the diagnosis of viral infection.

4 Claims, 6 Drawing Sheets

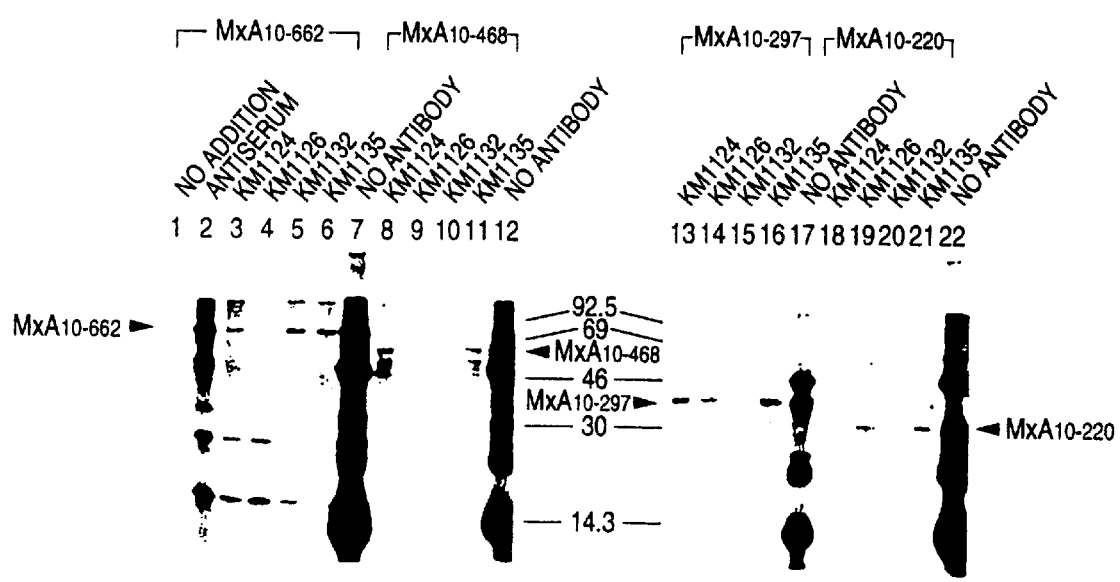

EXANTHEMA SUBITUM

HAND-FOOT-AND-MOUTH DISEASE

MUMPS

INFECTIOUS MONONUCLEOSIS

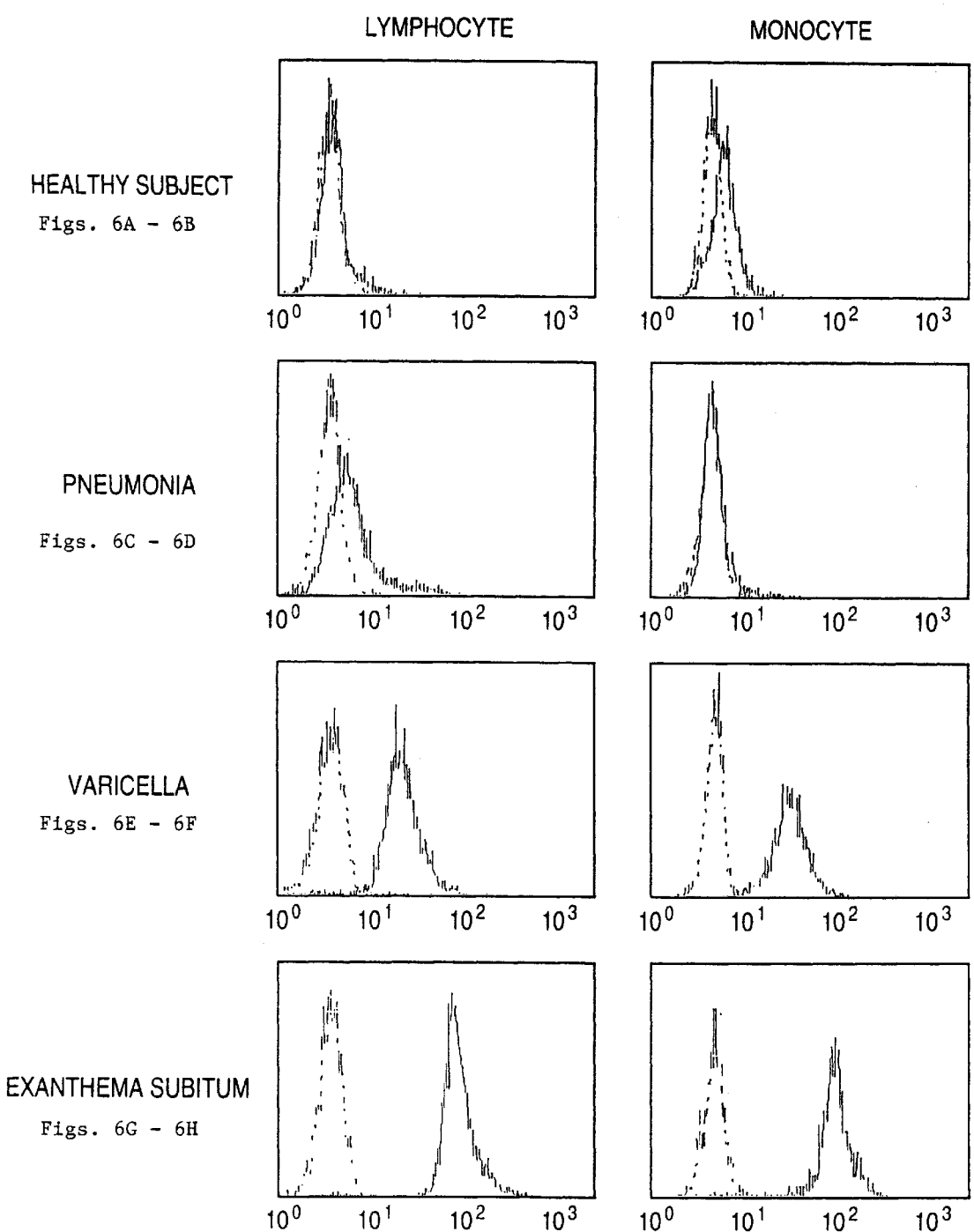

MONOCLONAL ANTIBODY TO HUMAN MX PROTEIN MXA

This application is a continuation of U.S. Ser. No. 08/628,612, filed Apr. 8, 1996, which is the national phase of PCT/JP95/01573, filed Aug. 8, 1995, now abandoned.

TECHNICAL FIELD

This invention relates to a monoclonal antibody specifically reactive with human Mx protein which is useful for the diagnosis of various diseases and to a hybridoma capable of producing the antibody.

BACKGROUND ART

It has been revealed by experiments using mice that Mx protein is induced when cells are stimulated with interferon, and that it is an important protein in exerting resistance to influenza virus infection [*Proc. Natl. Acad. Sci. USA,* 80, 1910–1914 (1983), *Cell,* 44, 147–158 (1986) and *Cell,* 62, 51–61 (1990)]. Thereafter, it was found that two types of protein, MxA and MxB, homologous to the mouse Mx protein, are also induced in human when cells are stimulated with interferon [*Mol. Cell. Biol.,* 9, 5062–5072 (1989) and *J. Virol.,* 64, 1171–1181 (1990)]. Infection experiments using influenza virus A and vesicular stomatitis virus have revealed that MxA inhibits viral growth in cells but MxB does not have the inhibition activity [*J. Virol.,* 64, 3370–3375 (1990)].

A monoclonal antibody to MxA was first prepared by immunizing mice with the purified protein [*J. Interferon Res.,* 7, 331–343 (1987)]. Thereafter, Towbin et al. prepared 5 monoclonal antibodies using recombinant MxA expressed in *Escherichia coli* as an immunogen [*J. Interferon Res.,* 12, 67–74 (1992)]. It was confirmed by enzyme immunoassay (ELISA) and Western blotting that the monoclonal antibodies of Towbin et al. reacted with MxA, and they could be divided into those which recognize an epitope corresponding to amino acids 1 to 429, counting from the N-terminus, and those which recognize another epitope corresponding to amino acids 430 to 662.

Recently, with the advance in studies on the structure and function of Mx protein, it has been revealed that the Mx protein has a GTP-binding domain and GTPase activity, which are now regarded as important factors in relation to the anti-virus activity [*Trends in Cell Biology,* 3, 268–272 (1993)]. Also, the possibility has been suggested that Mx protein has a self-assembly motif and forms a large complex body through association of its molecules making use of the motif, thereby exerting its anti-virus function [*J. Biol. Chem.,* 268, 15033–15038 (1993)].

Detailed elucidation of relationship between structure and function of Mx protein will make possible the accurate diagnosis of viral infectious conditions which are reflected by such a relationship. In the case of the known monoclonal antibodies which recognize MxA, it is difficult to elucidate the relationship of their functions with the GTP-binding domain and self-assembly motif because of the vague specificity of the binding site. Thus, accurate diagnosis of viral infectious conditions cannot be made. In addition, there are no reports of monoclonal antibodies capable of recognizing MxA which is intracellularly induced solely by viral infection, not by artificial stimulation with interferon.

The present invention relates to a monoclonal antibody which recognizes an epitope corresponding to amino acids 10 to 220, amino acids 221 to 297 or amino acids 469 to 662, counting from the N-terminus of a human Mx protein MxA, that specifically reacts with the human Mx protein by western blotting, immunoprecipitation or immunocyte staining and to a hybridoma which produces that antibody.

DISCLOSURE OF THE INVENTION

The following outlines the process for producing the anti-human Mx protein MxA monoclonal antibody of the present invention.

An MxA-encoding cDNA is cloned into a plasmid and introduced into *E. coli* cells in accordance with a known method [*J. Interferon Res.,* 12, 67–74 (1992)]. Since MxA is expressed and accumulated as intracellular granules in *E. coli,* the cells are disrupted, for example, by an ultrasonication and MxA is solubilized by treating the sonicate with a surface active agent or a protein denaturing agent. The solubilized MxA is purified by repeated centrifugation. Splenocytes of an animal immunized with the purified recombinant MxA are fused with mouse myeloma cells to obtain hybridoma strains from which a hybridoma strain capable of producing a monoclonal antibody that reacts with MxA but not with MxA-free protein contaminant derived from *E. coli* cells is subsequently selected. The selected hybridoma strain is cultured or administered to an animal to produce ascites tumor in the animal, and monoclonal antibodies are collected from the resulting culture medium or ascitic fluid. From the monoclonal antibodies obtained, those which specifically react with MxA by western blotting are selected. Also selected are those which positively stain interferon-stimulated cells and virus-infected cells when used as the first antibody of immunocyte staining.

The sites recognized by the monoclonal antibodies can be determined in the following manner.

The MxA gene is digested into small fragments using restriction enzymes in order to synthesize mRNA by in vitro transcription (*Molecular Cloning, A Laboratory Manual,* 2nd edition, published by Cold Spring Harbor Laboratory Press, 1989). Next, in vitro translation (*Molecular Cloning, A Laboratory Manual,* 2nd edition, published by Cold Spring Harbor Laboratory Press, 1989) is carried out in the presence of $^{35}$S-methionine to synthesize $^{35}$S-methionine-labeled protein fragments which are successively shortened from the C-terminal end. These labeled protein fragments are allowed to react with monoclonal antibodies, and the reaction products are precipitated, for example, using beads labeled with a second antibody. The precipitate is separated by SDS-polyacrylamide electrophoresis, and the molecular weight of the precipitated protein is measured by autoradiography. The binding site of each monoclonal antibody is determined based on the measured molecular weight.

Some of the monoclonal antibodies which recognize certain domains of the human Mx protein MxA can be used, for example, in the diagnosis of viral infectious conditions.

The process for producing the anti-human Mx protein MxA monoclonal antibody of the present invention is described in detail below.

(1) Preparation of Antigen

Recombinant MxA is obtained by transforming *E. coli* cells with an expression vector which contains MxA-encoding cDNA or MxA is purified from cultured cells stimulated with interferon or the like.

(2) Immunization of Animals and Preparation of Antibody-Producing Cells

Mice, rats or hamsters of 3 to 20 weeks of age are immunized with the antigen prepared in step (1) above, and antibody-producing cells are collected from the spleen, lymph node or peripheral blood of the animals. The immunization may be carried out by administering the antigen together with an appropriate adjuvant, such as complete Freund's adjuvant or aluminum hydroxide gel plus pertussis vaccine, to the animals subcutaneously, intravenously or intraperitoneally. Following the first antigen administration, the antigen is administered repeatedly 5 to 10 times at one- to two-week intervals. Three to seven days after each administration, a blood sample is taken from the venous plexus of the fundus of the eye, and the resulting serum is examined, for example, by enzyme-linked immunosorbent assay (*Antibodies—A Laboratory Manual,* Cold Spring Harbor Laboratory, 1988) to determine whether it is reactive with the antigen. Mice, rats or hamsters whose serum shows a sufficient antibody titer against the antigen used for immunization are submitted for use as a splenocyte source.

For submission to fusion between splenocytes and myeloma cells, the spleen of the immunized mouse, rat or hamster is excised 3 to 7 days after the final administration of the antigen and splenocytes are collected. That is, the spleen is cut into pieces in MEM medium (Nissui Pharmaceutical Co., Ltd.) and dissociated using forceps, and, after centrifugation (1,200 rpm, 5 minutes), the supernatant is discarded and the sediment is treated with Tris-ammonium chloride buffer (pH 7.65) for 1 to 2 minutes to eliminate erythrocytes and then washed three times with MEM medium and used as splenocytes for cell fusion.

(3) Preparation of Myeloma Cells

Mouse-derived established cell lines are used as the myeloma cells. For instance, the 8-azaguanine-resistant mouse (BALB/c-derived) myeloma cell lines P3-X63Ag8-U1 (P3-U1) [*Current Topics in Microbiology and Immunology,* 18, 1–7, (1978)], P3-NS1/1-Ag41 (NS-1) [*European J. Immunology,* 6, 511–519, (1976)], SP2/O-Ag14 (SP-2) [*Nature,* 276, 269–270, (1978)], P3-X63-Ag8653 (653) [*J. Immunology,* 123, 1548–1550, (1979)], P3-X63-Ag8 (X63) [*Nature,* 256, 495–497, (1975)] and the like may be used. These cell lines are subcultured in an 8-azaguanine medium [prepared by supplementing RPMI-1640 medium with glutamine (1.5 mM), 2-mercaptoethanol ($5 \times 10^{-5}$ M), gentamicin (10 μg/ml) and fetal calf serum (FCS) (to be referred to as "normal medium" hereinafter) and further supplementing the resulting medium with 8-azaguanine (15 μg/ml)], namely, 3 to 4 days before cell fusion, subculture is performed in the normal medium to ensure a cell number of not less than $2 \times 10^7$ cells on the day of cell fusion.

(4) Cell Fusion

The antibody-producing cells obtained by immunization as described in step (2) above and the myeloma cells obtained as described in step (3) above are washed well with the MEM medium or PBS (1.83 g of disodium phosphate, 0.21 g of monopotassium phosphate and 7.65 g of sodium chloride per liter of distilled water, pH 7.2), mixed in a ratio of antibody-producing cells:myeloma cells=5–10:1, and subjected to centrifugation (1,200 rpm, 5 minutes). The resulting supernatant is discarded and the precipitated cells are thoroughly disintegrated. A mixture consisting of 2 g of polyethylene glycol-1,000 (PEG-1,000), 2 ml of MEM and 0.7 ml of dimethyl sulfoxide is added to the cells with stirring to obtain 0.2 to 1 ml/$10^8$ antibody-producing cells at 37° C. One to 2 ml of MEM are added several times at 1- to 2-minute intervals, and then the whole amount is brought to 50 ml by the addition of MEM. After centrifugation (900 rpm, 5 minutes), the supernatant is discarded, the cells are loosened gently and then suspended in 100 ml of an HAT medium (prepared by supplementing the normal medium with hypoxanthine ($10^{-4}$ M), thymidine ($1.5 \times 10^{-5}$ M) and aminopterin ($4 \times 10^{-7}$ M)] by repeated drawing up into and discharging from a graduated pipette. This suspension is distributed in 100 μl portions into each well of 96 well incubation plates, and incubation is carried out in a 5% $CO_2$ incubator at 37° C. for 7 to 14 days.

After incubation, a portion of the culture supernatant is taken from each well and subjected, for example, to enzyme-linked immunosorbent assay to select those which react with MxA antigen but do not with MxA-free proteins. Thereafter, cloning is repeated twice by the limiting dilution method [using an HT medium (HAT medium minus aminopterin) for the first cloning and the normal medium for the second], thereby selecting strains for which a high antibody titer is constantly observed, as anti-human Mx protein MxA monoclonal antibody-producing hybridoma strains.

Illustrative examples of the anti-human Mx protein MxA monoclonal antibody-producing hybridoma strains include hybridoma cell lines KM1124, KM 1132, KM1135 and the like. The hybridoma cell lines KM1124, KM 1132 and KM1135 have been deposited, under the terms of the Budapest Treaty, with the National Institute of Bioscience and Human Technology 1–3, Higashi 1 chome Tsukuba-shi Ibaraki-ken, 305, Japan, Agency of Industrial Science and Technology, on Jul. 5, 1994, and have been assigned the accession numbers FERM BP-4729, FERM BP-4730 and FERM BP-4731, respectively.

(5) Preparation of Monoclonal Antibody

Each of the anti-human Mx protein MxA monoclonal antibody-producing hybridoma strains obtained in step (3) above is intraperitoneally injected into 8- to 10-week-old mice or nude mice treated with pristane [by intraperitoneal administration of 0.5 ml of 2,6,10,14-tetramethylpentadecane (pristane) followed by 2 weeks of feeding] at a dose of $2 \times 10^6$ to $5 \times 10^7$ cells per animal. The hybridoma causes ascites tumor development in 10 to 21 days. The ascitic fluid is collected from the mice, centrifuged (3,000 rpm, 5 minutes) to remove solid matter and, after salting out with 40–50% ammonium sulfate, subjected to purification by caprylic acid precipitation or using a DEAE-Sepharose column, a protein A column or a gel filtration column, followed by collection of IgG or IgM fractions to give a purified monoclonal antibody.

The subclass of the antibody can be determined by enzyme immunoassay using a subclass typing kit. The quantity of protein can be determined by the Lowry method, followed by calculation based on the absorbance at 280 nm.

(6) Western Blotting (Reaction with Recombinant MxA)

Reaction specificity of the anti-human Mx protein MxA monoclonal antibody selected in step (5) above is confirmed by western blotting.

A 1 to 10 μg portion of recombinant MxA expressed in *E.coli* or MxA purified from cells stimulated with interferon or the like is fractionated by SDS-polyacrylamide electrophoresis (*Antibodies—A Laboratory Manual,* Cold Spring Harbor Laboratory, 1988) and then blotted on a PVDF (polyvinylidene difluoride) membrane. After blocking with a BSA solution, it is allowed to react with 1 to 10 μg/ml of the culture supernatant of the anti-human Mx protein MxA monoclonal antibody or the purified antibody for 2 hours at room temperature or overnight at 4° C. After washing with PBS or PBS-Tween well, 1 to 50 µg/ml of an anti-mouse immunoglobulin antibody labeled with biotin, an enzyme, a chemiluminescent substance, a radioactive compound or the like, is dispensed in 50 to 100 µl/well portions and the reaction carried out at room temperature for 1 to 2 hours. After thorough washing, the reaction is carried out using each type of labeled second antibody to confirm that the anti-human Mx protein MxA monoclonal antibody reacts only with MxA and not with MxA-free proteins.

(7) Western Blotting (Reaction with Intracellular MxA)

Interferon a-stimulated cells are washed with PBS, suspended in a cytolysis buffer, allowed to stand for 1 to 10 hours at 4° C. and then centrifuged. The resulting supernatant is fractionated by SDS-polyacrylamide electrophoresis (*Antibodies—A Laboratory Manuals,* Cold Spring Harbor Laboratory, 1988) and then blotted on a PVDF membrane. After blocking with a BSA solution, the membrane is allowed to react with 1 to 10 µg/ml of the culture supernatant of the anti-human Mx protein MxA monoclonal antibody or the purified antibody for 2 hours at room temperature or overnight at 4° C. After thorough washing with PBS or PBS-Tween, 1 to 50 µg/ml of an anti-mouse immunoglobulin antibody labeled with biotin, an enzyme, a chemiluminescent substance, a radioactive compound or the like is dispensed in 50 to 100 µl/well portions and the reaction carried out at room temperature for 1 to 2 hours. After thorough washing, the reaction is carried out using each type of labeled second antibody to confirm that the anti-human Mx protein MxA monoclonal antibody reacts with MxA derived from cells stimulated with interferon α or the like.

(8) Immunocyte Staining (Detection of MxA Induced with Interferon α or the like)

A suspension of adherent type cultured cells is dispensed in 100 to 500 µl/well portions into chamber slides ($2 \times 10^4$ cells/well), stimulated with interferon α or the like and cultured overnight at 37° C. After washing with PBS, the cells are fixed with paraformaldehyde or the like. After further washing with PBS, the cells are treated with Triton X or the like in order to increase permeability of the antibody. After blocking using normal horse serum or the like, the cells are allowed to react with the culture supernatant of 1 to 10 µg/ml of anti-human Mx protein MxA monoclonal antibody or the purified antibody for 30 minutes at room temperature. After washing, 1 to 50 µg/ml of an anti-mouse immunoglobulin antibody labeled with a fluorescence dye is dispensed in 100 to 500 µl/well portions and the reaction carried out at room temperature for 30 minutes in the dark. After thorough washing, the cells are sealed with glycerol and observed under a fluorescence microscope to confirm that the monoclonal antibody reacts with cells stimulated with interferon α or the like but not with un-stimulated cells.

(9) Immunocyte Staining (Detection of MxA Induced by Viral Infection)

A suspension of adherent type cultured cells is dispensed in 100 to 500 µl/well portions into chamber slides ($2 \times 10^4$ cells/well), infected with influenza virus or the like virus and cultured overnight at 37° C. After washing with PBS, the cells are fixed with paraformaldehyde or the like. After further washing with PBS, the cells are treated with Triton X or the like in order to increase permeability of the antibody. After blocking with normal horse serum or the like, the cells are allowed to react with the culture supernatant of 1 to 10 µg/ml of anti-human Mx protein MxA monoclonal antibody or the purified antibody for 30 minutes at room temperature. After washing, 1 to 50 µg/ml of an anti-mouse immunoglobulin antibody labeled with a fluorescence dye is dispensed in 100 to 500 µl/well portions and the reaction carried out at room temperature for 30 minutes in the dark. After thorough washing, the cells are sealed with glycerol and observed under a fluorescence microscope to confirm that the monoclonal antibody reacts with cells infected with the virus but not with un-stimulated cells.

(10) Determination of Monoclonal Antibody Binding Domain

The MxA-encoding gene DNA is digested with several restriction enzymes and in vitro transcription is carried out in the presence of T7 RNA polymerase to synthesize several mRNA samples having different lengths. Next, in vitro translation is carried out using these mRNA samples in the presence of $^{35}$S-methionine to synthesize $^{35}$S-methionine-labeled protein fragments which are successively shortened from the C-terminal end. These labeled protein fragments are allowed to react with the anti-human Mx protein MxA monoclonal antibody at 4° C. for 1 to 4 hours. The reaction solution is mixed with beads labeled with a second antibody and a 1 hour reaction is carried out at 4° C. with shaking. The precipitate obtained by centrifugation is separated by SDS-polyacrylamide electrophoresis, and the molecular weight of the precipitated protein is measured by autoradiography. The binding site of the monoclonal antibody is determined based on the measured molecular weight.

Illustrative examples of the anti-human Mx protein MxA monoclonal antibody of the present invention include monoclonal antibodies KM1124, KM1132 and KM1135 produced by hybridoma cell strains KM1124, KM1132 and KM1135, respectively.

Since the anti-human Mx protein MxA monoclonal antibody of the present invention has the ability to react with MxA induced by viral infection, it can be used in the detection of viral infection.

BRIEF DESCRIPTION OF THE DRAWINGS

FIGS. 3A and B shows results of the autoradiography of $^{35}$S-methionine-labeled MxA protein fragments precipitated by the anti-human Mx protein MxA monoclonal antibody. Lanes 1 to 7 (FIG. 3A) represent immune precipitates of the anti-human Mx protein MxA monoclonal antibody with an MxA protein fragment of amino acids 10 to 662, counting from the N-terminus, lanes 8 to 12 (FIG. 3A) represent those with a protein fragment of amino acids 10 to 468, counting from the N-terminus, lanes 13 to 17 (FIG. 3B) represent those with a protein fragment of amino acids 10 to 297, counting from the N-terminus and lanes 18 to 22 (FIG. 3B) represent those with a protein fragment of amino acids 10 to 220, counting from the N-terminus. The anti-human Mx protein MxA monoclonal antibodies used herein are KM1124 in lanes 3, 8, 13 and 18, KM1126 in lanes 4, 9, 14 and 19, KM1132 in lanes 5, 10, 15 and 20 and KM1135 in lanes 6, 11, 16 and 21. Lane 1 shows results obtained in the absence of the MxA protein fragment and monoclonal antibody, lane 2 shows results obtained in the case of using rat anti-Mx protein MxA serum in place of the monoclonal antibody and lanes 7, 12, 17 and 22 show results obtained in the absence of the monoclonal antibody.

FIGS. 6A–H shows results of the reactivity of MxA with anti-human Mx protein MxA monoclonal antibody KM1135 on the surface of peripheral blood cells derived from a healthy person and patients infected with various viruses using a flow cytometer.

BEST MODE OF CARRYING OUT THE INVENTION

Examples

(1) Preparation of Antigen

Figure 1:
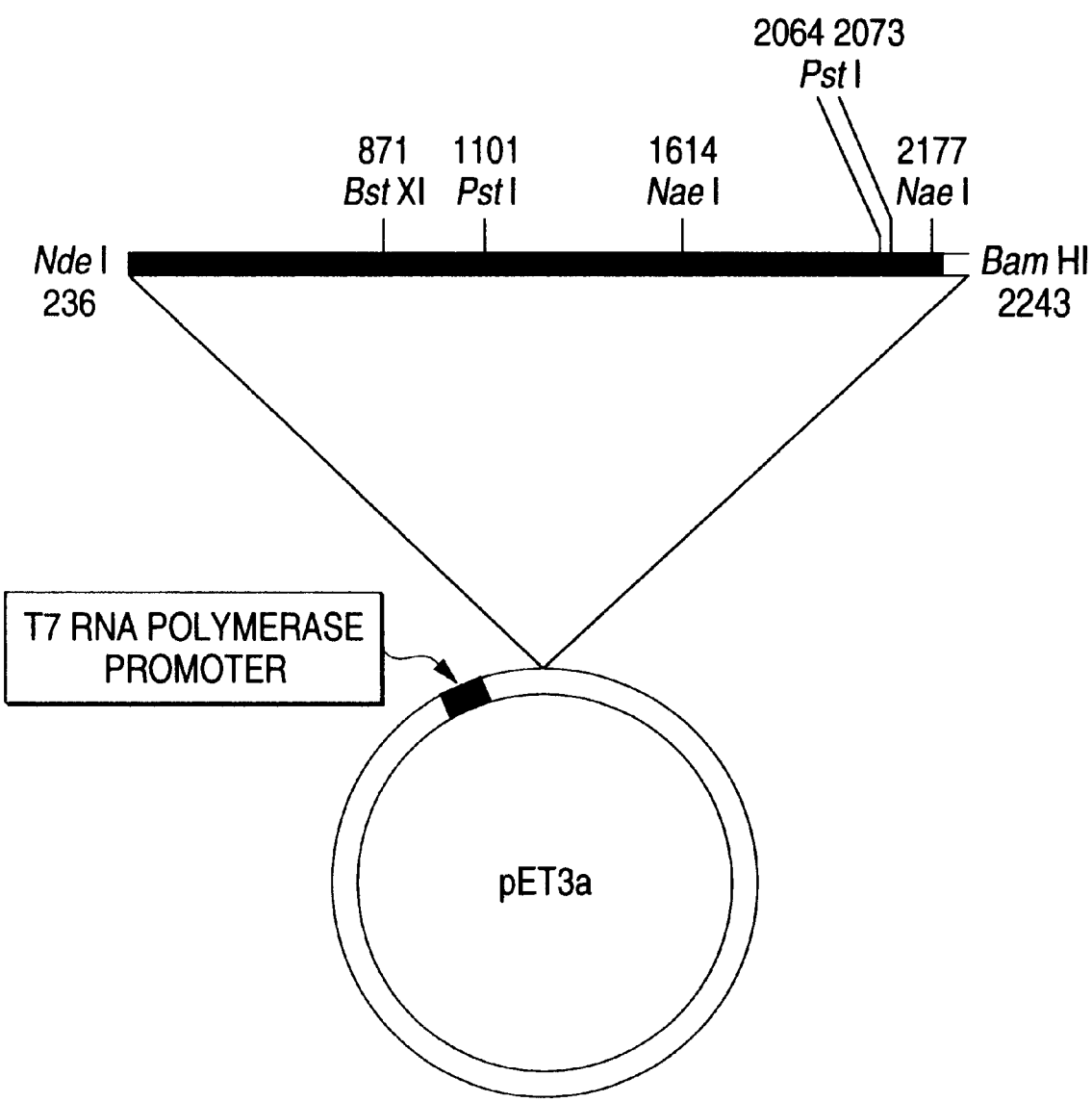
FIG. 1 shows structure of a vector for use in the expression of MxA in *E. coli.*

An expression vector containing MxA-encoding cDNA (FIG. 1) was introduced into *E. coli* cells in accordance with a known method (*Molecular Cloning, A Laboratory Manual*, 2nd edition, published by Cold Spring Harbor Laboratory Press, 1989), and the cells were cultured at 37° C. for 4 hours in 200 ml of LB medium (containing 200 µg/ml of ampicillin), followed by the addition of 0.5 mM of isopropylthiogalactoside (IPTG) and subsequent 2 hours of culturing at 37° C. A 200 ml portion of the cultured broth was centrifuged at 3,000×g for 15 minutes, and the precipitate containing *E. coli* cells was suspended in 100 ml of buffer solution 1 (10 mM Tris-HCl, 1 mM EDTA, 150 mM NaCl, pH 8). After centrifuging again, the precipitate was suspended in 7 ml of buffer solution 1 and subjected to an ultrasonic treatment to disrupt the cells. This was centrifuged at 10,000×g for 30 minutes, and the precipitate was suspended in 3.5 ml of buffer solution 2 (50 mM Tris-HCl, 10 mM EDTA, 100 mM NaCl, 0.5% Triton X-100, pH 7.9), allowed to stand for 5 minutes at 20° C. and then centrifuged again at 10,000×g for 15 minutes. After repeating this centrifugation step twice, the precipitate obtained was suspended in 3.5 ml of buffer solution 3 (50 mM Tris-HCl, 1 mM EDTA-200 mM KCl, 10 mM $MgCl_2$, 10 mM dithiothreitol, 20% glycerol, 6 M urea, pH 7.9), allowed to stand for 10 minutes at 0° C. and then centrifuged again at 10,000×g for 15 minutes. After repeating this centrifugation step twice, the precipitate obtained was again suspended in 2 ml of buffer solution 4 (10 mM Tris-HCl, 0.1 mM EDTA, 1 mM dithiothreitol, 6 M guanidine chloride, pH 7.9) and centrifuged at 10,000×g for 15 minutes to recover the solubilized protein in the supernatant. The supernatant was dialyzed twice against 1 liter of buffer solution 5 (50 mM Tris-HCl, 10 mM EDTA, 100 mM NaCl, 5% glycerol, 0.25% Triton X-100, pH 7.9). By this method, 2.5 mg of MxA was recovered from 200 ml of the *E. coli* culture broth.

(2) Immunization of Animals and Preparation of Antibody-Producing Cells

A 30 µg portion of MxA prepared in step (1) above, together with 2 mg of an aluminum gel and $1×10^9$ cells of pertussis vaccine (manufactured by Chiba Serum Institute), was administered to 5-week-old female mice (Balb/c) and, 2 weeks thereafter, 30 µg of MxA was administered once a week for 4 weeks. Blood was sampled from the venous plexus of the fundus of the eye and tested for serum antibody titer by the enzyme immunoassay described below, and, 3 days after the final immunization, the spleen was excised from a mouse showing a sufficient antibody titer.

The spleen was cut to pieces in MEM medium (manufactured by Nissui Pharmaceutical Co., Ltd.) and dissociated using forceps and, after centrifugation (1,200 rpm, 5 minutes), the supernatant was discarded and the sediment was treated with Tris-ammonium chloride buffer (pH 7.65) for 1 to 2 minutes to eliminate erythrocytes and then washed three times with the MEM medium and submitted for cell fusion.

Enzyme Immunoassay

A 1 to 50 µg/ml portion of MxA obtained in step (1) above or a 1% BSA solution was distributed in 10 to 100 µl portions into wells of a 96 well EIA plate (manufactured by Greiner), and the plate was kept overnight at 4° C. for antigen coating. Next, a PBS solution containing 1% BSA (BSA-PBS) was distributed in 100 to 200 µl portions into the wells, and the plate was kept at room temperature for 1 to 2 hours or at 4° C. for a night or two for blocking the protein-binding residues remaining on the plate. Thereafter, BSA-PBS was discarded, the plate was washed well with PBS, samples (mouse sera, hybridoma culture supernatants, purified monoclonal antibodies) diluted with BSA-PBS were distributed in 20 to 100 µl portions into the wells, each as a first antibody, and then the plate was kept at room temperature for 2 to 3 hours or at 4° C. overnight. After thorough washing with PBS or PBS-Tween, a peroxidase-labeled anti-mouse immunoglobulin antibody (manufactured by DAKO) was distributed as a second antibody in 50 to 100 µl portions into the wells, and the plate was kept at room temperature for 2 hours.

After thorough washing with PBS-Tween, color development was generated using an ABTS substrate solution [prepared by dissolving 550 mg of 2,2'-azinobis(3-ethylbenzothiazoline-6-sulfonic acid) diammonium salt in 1 liter of 0.1 M citrate buffer (pH 4.2) and adding, just prior to use, hydrogen peroxide to the solution to a concentration of 1 µl/ml], and absorbance at $OD_{415}$ nm was measured.

(3) Preparation of Mouse Myeloma Cells

An 8-azaguanine-resistant mouse myeloma cell line P3-U1 was cultured in the normal medium to ensure a cell number of not less than $2×10^7$ cells on the day of cell fusion.

(4) Preparation of Hybridoma

The mouse splenocytes obtained in step (2) above and the myeloma cells obtained in step (3) above were mixed in a ratio of 10:1 and subjected to centrifugation (1,200 rpm, 5 minutes), the resulting supernatant was discarded and the precipitated cells were thoroughly loosened. A mixture consisting of 2 g of polyethylene glycol-1,000 (PEG-1,000), 2 ml of MEM and 0.7 ml of dimethyl sulfoxide was added to the cells with stirring in an amount of 0.2 to 1 $ml/10^8$ mouse splenocytes at 37° C. One to 2 ml of MEM were added thereto several times at 1- to 2-minute intervals, and then the whole amount was brought to 50 ml by further addition of MEM. After centrifugation (900 rpm, 5 minutes), the supernatant was discarded and the cells were loosened gently and then gently suspended in 100 ml of an HAT medium by repeated drawing up into and discharging from a graduated pipette.

Figure 2A:
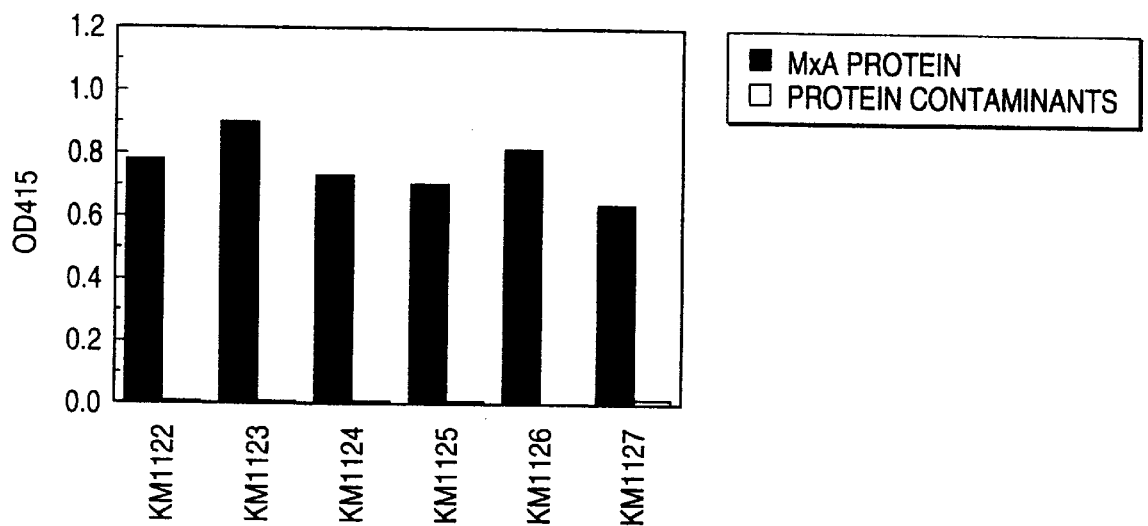
FIGS. 2A and B shows the reactivity of the anti-human Mx protein MxA monoclonal antibody with MxA and MxA-free protein impurities derived from *E. coil* cells.
Figure 2B:
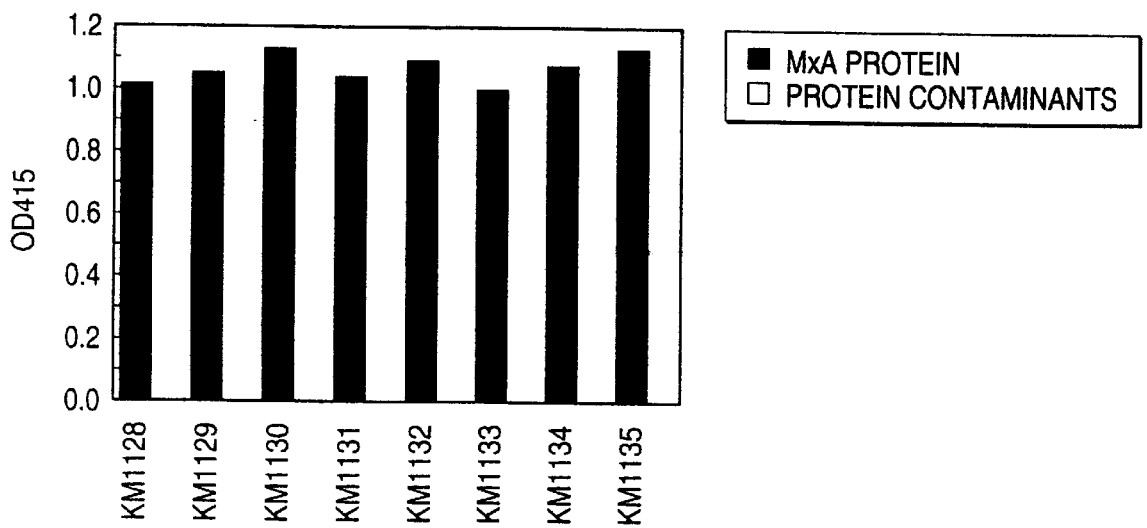

This suspension was distributed in 100 µl portions into each well of a 96 well incubation plate, and incubation is carried out in a 5% $CO_2$ incubator at 37° C. for 10 to 14 days. The culture supernatant was subjected to the enzyme immunoassay described in (1) to select those which reacted with MxA but not with MxA-free *E. coli*-originated protein impurities, and cloning was repeated twice by replacing the culture medium with HT medium and then with the normal medium, thereby obtaining a total of 14 anti-human Mx protein MxA monoclonal antibody-producing hybridoma cell lines KM1122, 1123, 1124, 1125, 1126, 1127, 1128, 1129, 1130, 1131, 1132, 1133, 1134 and 1135 (FIG. 2).

(5) Purification of Monoclonal Antibody

Each of the hybridoma cell lines obtained in step (4) above was intraperitoneally injected into pristane-treated 8-week-old nude mice (Balb/c) at a dose of 5 to $20\times10^6$ cells per animal. The hybridoma caused ascites tumor 10 to 21 days thereafter. The ascitic fluid was collected from the ascitic fluid-accumulated mice (1 to 8 ml/animal) and centrifuged (3,000 rpm, 5 minutes) to remove solid matter. This was subjected to purification by caprylic acid precipitation (*Antibodies—A Laboratory Manual*, Cold Spring Harbor Laboratory, 1988) to give purified monoclonal antibodies. Anti-human Mx protein MxA monoclonal antibodies obtained from the hybridoma cell lines KM1122, KM1123, KM1124, KM1125, KM1126, KM1127, KM1128, KM1129, KM1130, KM1131, KM1132, KM1133, KM1134 and KM1135 were named KM1122, KM1123, KM1124, KM1125, KM1126, KM1127, KM1128, KM1129, KM1130, KM1131, KM1132, KM1133, KM1134 and KM1135, respectively.

The subclass of the antibody was determined by enzyme immunoassay using a subclass typing kit. The subclass of each antibody is shown in Table 1.

TABLE 1

| Monoclonal antibody | Subclass | Monoclonal antibody | Subclass |
|---|---|---|---|
| KM1122 | G1 | KM1129 | G1 |
| KM1123 | G1 | KM1130 | G2a |
| KM1124 | G1 | KM1131 | G1 |
| KM1125 | G1 | KM1132 | G2a |
| KM1126 | G1 | KM1133 | G1 |
| KM1127 | G1 | KM1134 | G2a |
| KM1128 | G2a | KM1135 | G1 |

(6) Western Blotting (Reaction with Recombinant MxA)

Reaction specificity of each of the anti-human Mx protein MxA monoclonal antibodies obtained in step (5) above was examined by Western blotting as follows.

A 1 µg portion of MxA expressed in *E.coli* was fractionated by SDS-polyacrylamide electrophoresis (*Antibodies— A Laboratory Manual*, Cold Spring Harbor Laboratory, 1988) and then blotted on a PVDF membrane. After blocking with a BSA solution, the membrane was allowed to react with 10 µg/ml of each of the purified anti-human Mx protein MxA monoclonal antibodies for 2 hours at room temperature or over night at 4° C. After thorough washing with PBS-Tween, a peroxidase-labeled anti-mouse immunoglobulin antibody (manufactured by DAKO) was allowed to react at room temperature for 1 hour. After thorough washing, color development was effected using an HRP-Color Development Reagent substrate solution [prepared by dissolving 60 mg of HRP-Color Development Reagent (manufactured by Bio-Rad) in 20 ml of ice cold methanol, warming up the solution to room temperature and then adding thereto 100 ml of TBS buffer (2.42 g of Tris and 29.24 g of sodium chloride/1, pH 7.5), further adding 60 µl of hydrogen peroxide just prior to use]. As the result, it was confirmed that the anti-human Mx protein MxA monoclonal antibodies KM1122, KM1124, KM1126, KM1128, KM1129, KM1132 and KM1135 react only with MxA and not with MxA-free *E. coli*-originated protein impurities.

(7) Western Blotting (Reaction with Intracellular MxA)

Interferon α-stimulated human glioma T98G (ATCC CRL 1690) cells were washed with PBS, suspended in a cytolysis buffer [50 mM Tris-HCl (pH 7.2), 1% Triton X, 150 mM NaCl, 2 mM $MgCl_2$, 2 mM $CaCl_2$, 0.1% $NaN_3$, 50 mM iodoacetamide, 50 mM N-ethylmaleimide, 1 mg/ml leupepsin and 0.1 mM dithiothreitol], allowed to stand at 4° C. for 2 hours and then centrifuged. The thus obtained supernatant was fractionated by SDS-polyacrylamide electrophoresis (*Antibodies—A Laboratory Manual*, Cold Spring Harbor Laboratory, 1988) and then blotted on a PVDF membrane. After blocking with a BSA solution, the membrane was allowed to react with 10 µg/ml of each of the purified anti-human Mx protein MxA monoclonal antibodies for 2 hours at room temperature or overnight at 4° C. After thorough washing with PBS-Tween, a peroxidase-labeled anti-mouse immunoglobulin antibody (manufactured by DAKO) was allowed to react at room temperature for 1 hour. After thorough washing, color development was effected using the HAP-Color Development Reagent substrate solution. As a result, it was confirmed that the anti-human Mx protein MxA monoclonal antibodies KM1122, KM1124, KM1126, KM1128, KM1129, KM1132 and KM1135 react with MxA derived from the interferon α-stimulated cells.

(8) Immunocyte Staining (Reaction with Interferon-Induced MxA)

A suspension of human glioma T98G (ATCC CRL 1690) cells was dispensed in 500 µl portions into each well of an 8 well chamber slide ($2\times10^4$ cells/well), stimulated with interferon α (1,000 U/ml) and cultured overnight at 37° C. After washing with PBS, freshly prepared 4% paraformaldehyde was dispensed in 500 µl portions into each well and the cells were fixed at room temperature for 30 minutes. In order to increase permeability of the antibody through cell membranes, the cells were washed with PBS and treated at room temperature for 5 minutes with 0.1 to 0.2% Triton X-100 which was dispensed in 500 µl portions into each well. After dispensing 10% normal horse serum which was dispensed in 500 µl portions into each well, blocking was carried out at room temperature for 30 minutes, the cells were allowed to react with 10 µg/ml of each of the purified anti-human Mx protein MxA monoclonal antibodies for 30 minutes at room temperature. After washing with PBS, an FITC-labeled anti-mouse immunoglobulin antibody (manufactured by Wako Pure Chemical Industries) was dispensed in 200 µl portions into each well to react at room temperature for 30 minutes in the dark. After thorough washing with PBS, the cells were sealed with glycerol and observed under a fluorescence microscope. As a result, it was confirmed as shown in Table 2 that the anti-human Mx protein MxA monoclonal antibodies KM1124, KM1126, KM1132 and KM1135 react with the interferon α-stimulated cells but not with unstimulated cells.

TABLE 2

| Antibody | T98G cells | IFN-α stimulated T98G cells |
| --- | --- | --- |
| KM1122 | + | ++ |
| KM1124 | ± | ++ |
| KM1126 | − | + |
| KM1128 | ± | ± |
| KM1129 | − | ± |
| KM1132 | − | + |
| KM1135 | − | + |

++: strong reaction
+: reaction
±: weak reaction
−: no reaction (9) Immunocyte Staining (Reaction with MxA Induced by Viral Infection)

A suspension of human glioma T98G (ATCC CRL 1690) cells was dispensed in 500 μl portions into each well of an 8 well chamber slide (2×10⁴ cells/well), infected with influenza virus and cultured overnight at 37° C. After washing with PBS, freshly prepared 4% paraformaldehyde was dispensed in 500 μl portions into each well and the cells were fixed at room temperature for 30 minutes. In order to increase permeability of the antibody through cell membranes, the cells were washed with PBS and treated at room temperature for 5 minutes with 0.1 to 0.2% Triton X-100 which was dispensed in 500 μl portions into each well. After dispensing 10% normal horse serum in 500 μl portions into each well, blocking was carried out at room temperature for 30 minutes and the cells were allowed to react with 10 μg/ml of each of the purified anti-human Mx protein MxA monoclonal antibodies for 30 minutes at room temperature. After washing with PBS, an FITC-labeled anti-mouse immunoglobulin antibody (Wako Pure Chemical Industries) was dispensed in 200 μl portions into each well and the reaction carried out at room temperature for 30 minutes in the dark. After completion of the reaction, the cells were thoroughly An washed with PBS, sealed with glycerol and then observed under a fluorescence microscope. As a result, it was confirmed, as shown in Table 3, that the anti-human Mx protein MxA monoclonal antibodies KM1124 and KM1135 react with the virus-infected cells but not with unstimulated cells.

TABLE 3

| Antibody | T98G cells | Influenza infected T98G cells |
| --- | --- | --- |
| KM1124 | − | + |
| KM1132 | − | − |
| KM1135 | − | + |

(10) Determination of Monoclonal Antibody Binding Domain

Figures 4A, 4B:
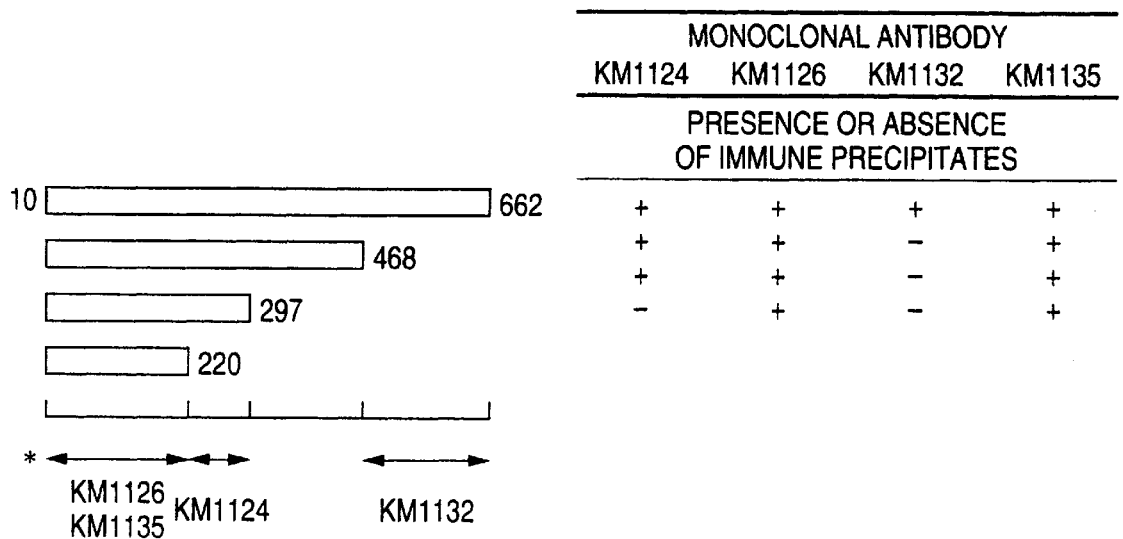
FIGS. 4A and B shows the presence or absence of the formation of immune precipitates of the anti-human Mx protein MxA monoclonal antibodies KM1124, KM1126, KM1132 and KM1135 with each MxA protein fragment and the binding site of each monoclonal antibody on MxA. The ranges indicated by arrows represent locations of the binding sites of the anti-human Mx protein MxA monoclonal antibodies KM1124, KM1126, KM1132 and KM1135.
Figure 5A:
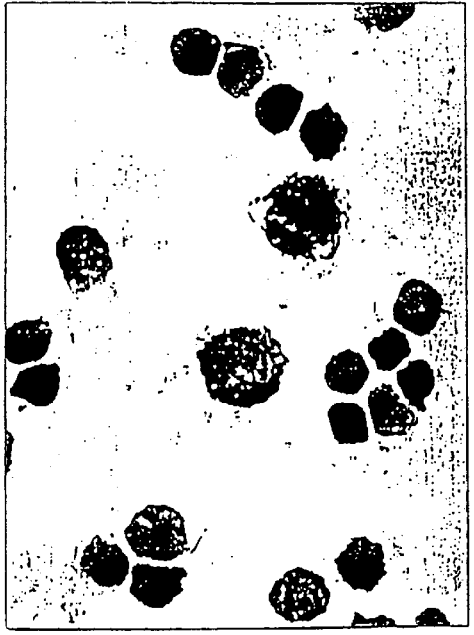
FIGS. 5A to D shows expression of the MxA protein in peripheral blood mononuclear cells originated from patients of exanthema subitum (FIG. 5A), hand-foot-and-mouth disease (FIG. 5B), mumps (FIG. 5C) and infectious mononucleosis (FIG. 5D).
Figure 5B:
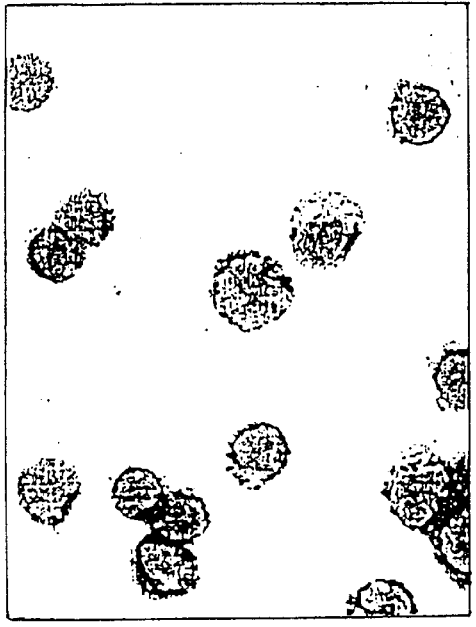
Figure 5C:
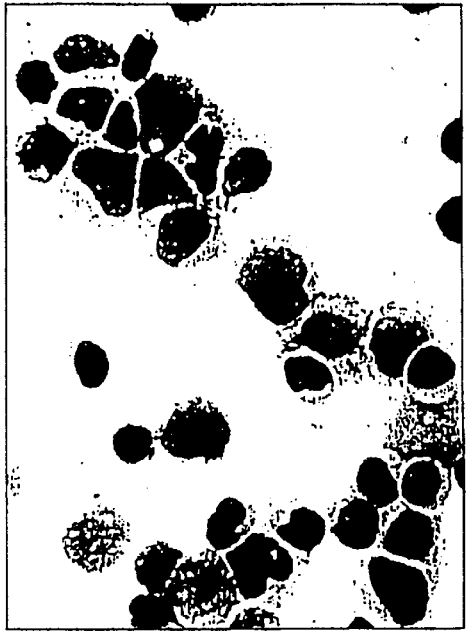
Figure 5D:
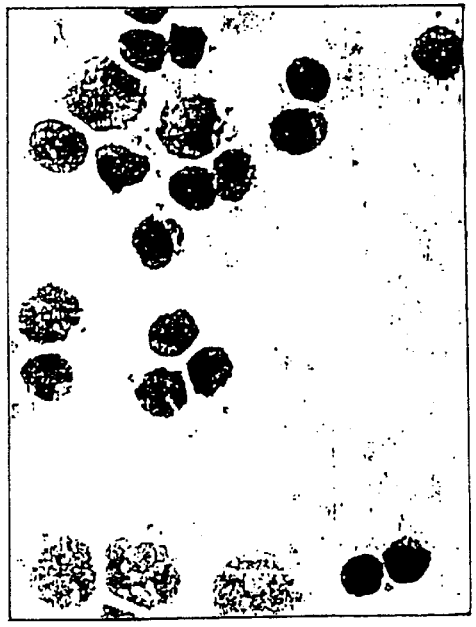

The MxA-encoding DNA was digested with restriction enzymes BstXI, PstI, NaeI and BamHI in the usual way and subjected to in vitro transcription (*Molecular Cloning, A Laboratory Manual,* 2nd edition, published by Cold Spring Harbor Laboratory Press, 1989) in the presence of T7 RNA polymerase to synthesize several mRNA samples having different lengths. Next, in vitro translation was carried out using these mRNA samples in the presence of $^{35}$S-methionine to synthesize $^{35}$S-methionine-labeled protein fragments which were successively shortened from the C-terminal end. The in vitro translation was carried out using reticulocyte lysate (#L416A, manufactured by Promega) in accordance with the manual attached thereto. As a result, labeled protein fragments corresponding to amino acids 10 to 662, amino acids 10 to 468, amino acids 10 to 297 and amino acids 10 to 220, counting from the N-terminus of MxA, were synthesized. Each of these labeled protein fragments was allowed to react with each of the anti-human Mx protein MxA monoclonal antibodies (1.25 μl of 1 mg/ml solution was used) in a reaction buffer (50 mM Tris-HCl, 1% NP-40, 0.2% BSA, pH 8.0) at 4° C. for 1 hour. The reaction solution was mixed with 40 μl of second antibody-labeled beads (#AG-005, manufactured by E. Y. Labo, 2-fold dilution) and the reaction carried out at 4° C. for an hour with shaking. This was subjected to centrifugation at 4° C. for 15 seconds and at 10,000×g, and the precipitate obtained was separated by an SDS-polyacrylamide electrophoresis and the molecular weight of the precipitated protein was determined by autoradiography (using X-ray films manufactured by Fuji Medical). The results are shown in FIG. 3. The binding site of each monoclonal antibody was determined based on the measured molecular weight (FIG. 4). As a result, it was revealed that the anti-human Mx protein MxA monoclonal antibodies KM1126 and KM1135 have a binding site at amino acids 10 to 220, and KM1124 at amino acids 220 to 297 and KM1132 at amino acids 468 to 662, counting from the amino terminus of MxA.

(11) Immunocyte Staining (Reaction with Interferon α-Induced MxA—Periodical Changes—)

A cell suspension (2×10⁴ cells/ml) of an adherent type cell line (human glioma T98G, ATCC CRL 1690) was dispensed in 500 μl portions into each well of an 8 well chamber slide, and the cells were cultured overnight at 37° C., stimulated with interferon α (1,000 U/ml) and again cultured at 37° C. for 0 to 6 hours. After washing with PBS, freshly prepared 4% paraformaldehyde was dispensed in 500 μl portions into each well and the cells were fixed at room temperature for 30 minutes. In order to increase permeability of the antibody through cell membranes, the cells were washed with PBS and treated at room temperature for 5 minutes with 0.2% Triton X-100 which was dispensed in 500 μl portions into each well. After blocking at room temperature for 30 minutes using 10% normal horse serum which was dispensed in 500 μl portions into each well, 10 μg/ml of each of the purified anti-human Mx protein MxA monoclonal antibodies KM1124, KM1132 and KM1135 was dispensed in 200 μl portions into each well and allowed to react at room temperature for 30 minutes. After washing with PBS, an FITC-labeled anti-mouse immunoglobulin antibody (Wako Pure Chemical Industries) was dispensed in 200 μl portions into each well and the reaction carried out at room temperature for 30 minutes in the dark. After thoroughly washing with PBS, the cells were sealed with glycerol and observed under a fluorescence microscope. As a result, it was revealed as shown in Table 4 that the antibodies KM1124, KM1132 and KM1135 could detect MxA induced by interferon α.

TABLE 4

| | IFN α induction time (hour) | | | |
|---|---|---|---|---|
| | 0 | 2 | 4 | 6 |
| KM1124 | + | + | + | + |
| KM1132 | − | ± | ± | + |
| KM1135 | − | ± | + | + |

+: reaction
±: weak reaction
−: no reaction

(12) Immunocyte Staining (Reaction with Viral Infection-Induced MxA—Periodical Changes—)

A cell suspension ($2 \times 10^4$ cells/ml) of an adherent type cell line (human glioma T98G, ATCC CRL 1690) was dispensed in 500 μl portions into each well of an 8 well chamber slide, and the cells were cultured overnight at 37° C., infected with influenza virus and again cultured at 37° C. for 0 to 8 hours. After washing with PBS, freshly prepared 4% paraformaldehyde was dispensed in 500 μl portions into each well and the cells were fixed at room temperature for 30 minutes. In order to increase permeability of the antibody through cell membranes, the cells were washed with PBS and treated at room temperature for 5 minutes with 0.2% Triton X-100 which was dispensed in 500 μl portions into each well. After blocking at room temperature for 30 minutes using 10% normal horse serum which was dispensed in 500 μl portions into each well, 10 μg/ml of each of the purified anti-human Mx protein MxA monoclonal antibodies KM1124, KM1132 and KM1135 was dispensed in 200 μl portions into each well and allowed to react at room temperature for 30 minutes. After washing with PBS, an FITC-labeled anti-mouse immunoglobulin antibody (Wako Pure Chemical Industries) was dispensed in 200 μl portions into each well and the reaction carried out at room temperature for 30 minutes in the dark. After thoroughly washing with PBS, the cells were sealed with glycerol and observed under a fluorescence microscope. As a result, it was revealed as shown in Table 5 that the antibodies KM1124, KM1132 and KM1135 could detect MxA induced by viral infection.

TABLE 5

| | Influenza virus infection time (hour) | | | | |
|---|---|---|---|---|---|
| | 0 | 2 | 4 | 6 | 8 |
| KM1124 | + | + | + | + | + |
| KM1132 | − | − | − | − | ± |
| KM1135 | − | − | − | ± | + |

+: reaction
±: weak reaction
−: no reaction

(13) Immunocyte Staining (Reaction with Virus-Induced MxA)

Exanthema subitum, hand-foot-and-mouth disease, mumps and infectious mononucleosis are viral diseases mainly found in children. Peripheral blood mononuclear cells were isolated from patients of these diseases with the aid of Lympho Prep to prepare cytospin samples. Each sample was fixed with acetone at 4° C. (for 20 minutes or more), dried and then soaked in 10% bovine serum albumin-containing TBS [0.05 M Tris-HCl buffer (pH 7.6)]. Anti-human Mx protein MxA monoclonal antibody KM1135 (20 μg/ml) which had been diluted with 10% rabbit serum-containing TBS was allowed to react at room temperature for 30 minutes, and the sample was then washed with TBS. This was allowed to react at room temperature for 30 minutes with a rabbit anti-mouse antibody (manufactured by DAKO) as the second antibody and then washed with TBS. This was allowed to react with a mouse monoclonal APAAP complex (DAKO) for 30 minutes at room temperature, washed with TBS, color generated using an alkaline phosphatase chromogenic substrate reagent (DAKO) and then observed under a microscope. As a result, all of the peripheral blood mononuclear cells isolated from the patients were stained positive as shown in FIG. 5.

(14) Flow Cytometry (Reaction with Virus-Induced MxA)

Peripheral blood mononuclear cells ($1 \times 10^6$ to $10^7$) isolated from a healthy person or patients were suspended in PBS, centrifuged at 500×g for 3 minutes and then fixed with 4% paraformaldehyde at room temperature for 15 minutes. After washing with PBS, the cells were treated at room temperature for 5 minutes with Triton X-100 which had been diluted to 0.1% with TBS containing 0.1% bovine serum albumin. After washing twice with a washing buffer (PBS containing 1% fetal bovine serum and 0.1% sodium azide), a 2.5 μl portion of anti-human Mx protein MxA monoclonal antibody KM1135 (20 μg/ml) was added to a 100 μl portion of the cell preparation solution and reacted for 20 minutes on ice. After washing twice with the washing buffer, reaction for 20 minutes with FITC-labeled anti-mouse IgG antibody (manufactured by Zymed, 1,000-fold dilution) on ice was carried out. After washing twice with the washing buffer, measurement was carried out using a flow cytometer. As a result, as shown in FIG. 6, peripheral blood mononuclear cells isolated from the healthy person and bacteria-infected patients did not react or reacted weakly with KM1135, while peripheral blood mononuclear cells isolated from the virus-infected patients reacted strongly with KM1135.

INDUSTRIAL APPLICABILITY

The present invention provides human Mx protein MxA monoclonal antibodies useful for instance in the diagnosis of viral infectious conditions.

What is claimed is:

1. A monoclonal antibody KM1135, Accession Number FERM BP-4731, which binds to an eptitope corresponding to amino acids 10 to 220, counting from the N-terminus of a human Mx protein MxA, specifically reacts with the human Mx protein by western blotting, immunoprecipitation or immunocyte staining, and belongs to IgG1 subclass.

2. A hybridoma which produces the monoclonal antibody of claim 1.

3. A monoclonal antibody KM1124, Accession Number FERM BP-4729, which binds to an eptitope corresponding to amino acids 221 to 297, counting from the N-terminus of a human Mx protein MxA, specifically reacts with the human Mx protein by western blotting, immunoprecipitation or immunocyte staining, and belongs to IgG1 subclass.

4. A hybridoma which produces the monoclonal antibody of claim 3.

* * * * *

UNITED STATES PATENT AND TRADEMARK OFFICE
CERTIFICATE OF CORRECTION

PATENT NO. : 6,180,102 B1  Page 1 of 1
DATED : January 30, 2001
INVENTOR(S) : Hanai It is certified that error appears in the above-identified patent and that said Letters Patent is hereby corrected as shown below:

Column 14,
Line 48, after "KM1135," insert -- , produced by hybridoma KM1135 --.
Line 54, after "hybridoma" insert -- KM1135, Accession Number FERM BP-4731, --.
Line 56, after "KM1124" insert -- produced by hybridoma KM1124 --.
Line 62, after "hybridoma" insert -- KM1124, Accession Number FERM BP-4729, --.

Signed and Sealed this

Twenty-first Day of May, 2002

Attest:

JAMES E. ROGAN
Attesting Officer  Director of the United States Patent and Trademark Office